(12) United States Patent
Heilek et al.

(10) Patent No.: US 7,589,236 B2
(45) Date of Patent: Sep. 15, 2009

(54) PROCESS FOR SEPARATING ACRYLIC ACID AND BENZOIC ACID PRESENT IN A PRODUCT GAS MIXTURE OF A PARTIAL HETEROGENEOUSLY CATALYZED GAS PHASE OXIDATION OF A $C_3$ PRECURSOR COMPOUND OF ACRYLIC ACID

(75) Inventors: Joerg Heilek, Bammental (DE); Klaus Joachim Mueller-Engel, Stutensee (DE); Martin Dieterle, Ludwigshafen (DE); Armin Diefenbacher, Freisbach (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/873,883

(22) Filed: Oct. 17, 2007

(65) Prior Publication Data

US 2008/0097123 A1     Apr. 24, 2008

Related U.S. Application Data

(60) Provisional application No. 60/852,674, filed on Oct. 19, 2006.

(30) Foreign Application Priority Data

Oct. 19, 2006   (DE) .................. 10 2006 049 939

(51) Int. Cl.
    *C07C 51/42*   (2006.01)
(52) U.S. Cl. ..................................... 562/600
(58) Field of Classification Search .................. None
    See application file for complete search history.

(56) References Cited

U.S. PATENT DOCUMENTS

| | | | |
|---|---|---|---|
| 5,198,578 A | 3/1993 | Etzkorn et al. | |
| 5,831,124 A | 11/1998 | Machammer et al. | |
| 6,433,222 B1 * | 8/2002 | Eck et al. | 562/600 |
| 6,448,439 B1 * | 9/2002 | Eck et al. | 562/600 |
| 6,679,939 B1 | 1/2004 | Thiel et al. | |
| 6,939,991 B2 | 9/2005 | Thiel et al. | |
| 7,179,875 B2 | 2/2007 | Fuchs et al. | |
| 7,238,827 B2 | 7/2007 | Hechler et al. | |
| 7,326,802 B2 | 2/2008 | Hechler et al. | |
| 7,348,443 B2 | 3/2008 | Proll et al. | |
| 2003/0060661 A1 | 3/2003 | Eck et al. | |
| 2004/0116741 A1 | 6/2004 | Nordhoff et al. | |
| 2004/0242826 A1 | 12/2004 | Nishimura | |
| 2005/0222459 A1 | 10/2005 | Nordhoff et al. | |
| 2007/0088092 A1 * | 4/2007 | Klanner et al. | 518/726 |
| 2007/0276157 A1 * | 11/2007 | Machhammer et al. | 562/545 |

FOREIGN PATENT DOCUMENTS

| | | |
|---|---|---|
| DE | 35 21 458 A1 | 12/1985 |
| DE | 197 40 252 A1 | 3/1999 |
| DE | 199 24 532 A1 | 11/2000 |
| DE | 101 31 297 A1 | 1/2003 |
| DE | 103 36 386 A1 | 3/2004 |
| DE | 102 45 585 A1 | 4/2004 |
| DE | 102 46 119 A1 | 4/2004 |
| DE | 102 47 240 A1 | 4/2004 |
| EP | 0 792 867 A2 | 9/1997 |
| EP | 0 990 636 B1 | 9/2003 |
| EP | 1 159 249 B1 | 4/2004 |
| EP | 1 484 303 A2 | 12/2004 |
| EP | 1 484 308 A1 | 12/2004 |
| EP | 1 484 309 A1 | 12/2004 |
| EP | 1 015 410 B2 | 9/2007 |
| GB | 2 160 543 A | 12/1985 |
| WO | WO 99/14181 | 3/1999 |
| WO | WO 00/05188 | 2/2000 |
| WO | WO 01/77056 A1 | 10/2001 |
| WO | WO 02/055469 A1 | 7/2002 |
| WO | WO 03/014172 A2 | 2/2003 |
| WO | WO 03/078378 A1 | 9/2003 |

* cited by examiner

*Primary Examiner*—Karl J Puttlitz
(74) *Attorney, Agent, or Firm*—Oblon, Spivak, McClelland, Maier & Neustadt, P.C.

(57) ABSTRACT

A process for separating acrylic acid and benzoic acid present in the product gas mixture of a partial oxidation to acrylic acid, in which the acrylic acid and the benzoic acid are first converted to a liquid phase, constituents having a lower boiling point than benzoic acid and acrylic acid are removed therefrom by thermal separating processes, and the acrylic acid is removed by crystallization from the remaining liquid phase.

22 Claims, No Drawings

PROCESS FOR SEPARATING ACRYLIC ACID AND BENZOIC ACID PRESENT IN A PRODUCT GAS MIXTURE OF A PARTIAL HETEROGENEOUSLY CATALYZED GAS PHASE OXIDATION OF A $C_3$ PRECURSOR COMPOUND OF ACRYLIC ACID

The present invention relates to a process for separating acrylic acid and benzoic acid present as the main product and by-product as well as other product gas mixture constituents in a product gas mixture of a partial heterogeneously catalyzed gas phase oxidation of a $C_3$ precursor compound of acrylic acid, in which the acrylic acid and the benzoic acid, together with other constituents of the product gas mixture which have lower and higher boiling points than acrylic acid, are converted from the product gas mixture to a liquid phase P, and constituents having a lower boiling point than benzoic acid and acrylic acid are removed from the resulting liquid phase P using at least one thermal separating process to leave a liquid phase P* which comprises at least 80% by weight of acrylic acid and, based on the amount of acrylic acid present, at least 0.1% by weight of benzoic acid.

Acrylic acid is an important monomer which finds use as such and/or in the form of its alkyl esters for obtaining polymers used in the hygiene sector (for example water-superabsorbing polymers) (cf. for example WO 02/055469 and WO 03/078378).

Acrylic acid can be prepared, for example by heterogeneously catalyzed partial oxidation of a $C_3$ precursor compound (propylene, propane and/or acrolein) (cf., for example EP-A 990636, U.S. Pat. No. 5,198,578, EP-A 1015410, EP-A 1484303, EP-A 1484308, EP-A 1484309 and US-A 2004/0242826).

The $C_3$ precursor compound used is, appropriately from an application point of view, generally a $C_3$ precursor compound of comparatively high purity (cf. DE-A 10131297). However, it is relatively inconvenient and costly to obtain, for example, crude propylene of such purity, and this generally involves various purification stages in order to isolate the $C_3$ precursor compound of acrylic acid in high purity (cf. DE-A 3521458). According to DE-A 12246119 and DE-A 10245585, the procedure should in particular be such that the resulting reaction gas mixture for the partial oxidation comprises as far as possible no $C_4$ hydrocarbons as undesired impurities which impair the catalyst performance. A disadvantage of such a procedure is that the aforementioned purification stages are complicated, which is why they are in some cases employed only with comparatively limited separating action for the purposes of an economically viable crude $C_3$ precursor compound (e.g. crude propylene).

Thorough in-house investigations have now shown that, when the crude $C_3$ precursor compound (e.g. the crude propylene) used for the heterogeneously catalyzed partial oxidation of the $C_3$ precursor compound (e.g. of the propylene) still comprises butadiene or compounds which can be converted to butadiene in the course of the partial oxidation, benzoic acid can be formed as a by-product of acrylic acid formation. The cause to which the benzoic acid formation can be attributed is presumably Diels-Alder reactions of the butadiene with $C_3$ dienophiles such as propylene, acrolein and acrylic acid which are present in the reaction gas mixture of the heterogeneously catalyzed partial oxidation, which are probably followed by a heterogeneously catalyzed oxydehydrogenation of the adduct to the aromatic. The latter is presumably catalyzed by the same catalysts as the actual target gas phase oxidation. If appropriate, a slight contamination of the crude $C_3$ precursor compound (for example of the crude propylene) with o-xylene may also be the cause of benzoic acid by-product formation. The use of multimetal oxide catalysts with elevated activity (or of catalyst charges whose volume-specific activity increases at least once in the direction of an increasing reactant conversion), additional use of steam as an inert diluent gas and an excess of molecular oxygen relative to the $C_3$ compounds to be oxidized partially in the particular oxidation steps (e.g. propylene→acrylic acid) appear to promote benzoic acid by-product formation, as do elevated reaction temperatures and conversions of the particular $C_3$ precursor compound in the particular oxidation stage (for example of the propylene in the first oxidation stage of a two-stage partial oxidation of propylene to acrylic acid, or of acrolein in the second oxidation stage of a partial oxidation of propylene to acrylic acid, or of the acrolein in an independent acrolein partial oxidation to acrylic acid, or of the propane in a one-stage partial oxidation of propane to acrylic acid). The aforementioned assumptions are supported by the fact that, in many cases, only benzaldehyde but not benzoic acid is found as a by-product of acrylic acid formation. Conversely, benzoic acid is generally accompanied by benzaldehyde as an acrylic acid by-product.

Both benzaldehyde and benzoic acid are undesired companions of acrylic acid. They are undesired because they are not entirely harmless as comparatively reactive aromatic compounds (this applies correspondingly to the esters of benzoic acid). When the acrylic acid and/or their alkyl esters obtained are used, therefore, to prepare polymers which find use in the hygiene sector (for example, water-absorbing polymers in diapers), it is necessary to ensure that the acrylic acid used and/or the alkyl acrylates used are scrupulously free of benzoic acid and benzaldehyde.

It is common knowledge that acrylic acid can be removed from the product gas mixture of the heterogeneously catalyzed partial gas phase oxidation of a $C_3$ precursor compound of acrylic acid (e.g. of propylene) by a combination of different separating processes. The combination employed in the specific case is generally dependent on the type and amount of the secondary components other than acrylic acid which are present in the product gas mixture, and upon the desired purity of the acrylic acid, which is generally guided by the particular use of the acrylic acid.

An essential constituent of such combinations of different separating processes is normally formed by thermal separating processes. The thermal separating processes are those in which gaseous (ascending) and liquid (descending) streams are conducted in countercurrent in separating columns comprising separating internals, heat and mass transfer taking place owing to the gradients existing between the streams and ultimately causing the separation desired in the separating column.

Examples of such thermal separating processes are (partial) condensation, fractional condensation (cf. DE-A 19924532) and rectification. The resulting separating action is based here in particular on the difference of the boiling points of acrylic acid and the secondary components other than acrylic acid. A further example is that of absorption. The separating action is based here in particular on the different solubility of acrylic acid and the secondary components other than acrylic acid in the absorption liquid. The above is also true of the thermal separating processes of stripping (a stripping gas absorbs, from a liquid, components with different affinity present in dissolved form therein) and desorption (the reverse process of absorption; the substances dissolved in the liquid phase are removed by lowering the partial pressure). The term "thermal separating processes" also comprises azeotropic distillation and rectification (they utilize the differing tendency of acrylic acid and the secondary components (the constituents other than acrylic acid in the reaction gas mixture of the partial oxidation) to form azeotropes with added azeotroping agents).

The boiling point difference between acrylic acid (141° C. at 1 atm) and benzaldehyde (178.1° C. at 1 atm) is generally insufficient to remove the benzaldehyde quantitatively from acrylic acid with an appropriate level of complexity using the aforementioned thermal separating processes. Instead, the latter removal is normally achieved only when the differing reactivity of benzaldehyde and acrylic acid with so-called aldehyde scavengers (WO 03/014172) for example aminoguanidine hydrogencarbonate, is additionally utilized. The reaction of the aldehyde with the aldehyde scavenger forms a new secondary component whose boiling point deviates to a significantly greater extent from the boiling point of acrylic acid than is the case in the case of the aldehyde itself, so that, on completion of reaction with the aldehyde scavenger, a quantitative removal can be achieved in a simple manner by a rectificative route. As an alternative, EP-A 1159249 discloses the separation of benzaldehyde and acrylic acid present in the product gas mixture of the partial oxidation by the combination of a thermal separating process (fractional condensation) and a crystallization (suspension crystallization) (cf. also DE-A 10247240).

In contrast to the above, the boiling point difference between acrylic acid (141° C. at 1 atm) and benzoic acid (250° C. at 1 atm) is so great that the use of a thermal separating process whose separating action is based on the different boiling points of the mixture constituents is normally accompanied by a quantitative separation of acrylic acid and benzoic acid (cf. DE-A 10336386, DE-A 19740252, DE-A 10247240) (further secondary components are frequently removed by crystallization after the benzoic acid removal). However, a disadvantage of such a thermal separation is that the fraction comprising the acrylic acid in enriched form has to be withdrawn from the separating column comprising separating internals above the feed of the mixture to be separated into the separating column. However, this is a thermally very demanding undertaking, since evaporation of the total amount of acrylic acid is energetically comparatively demanding (high boiling point, high enthalpy of evaporation, multiple evaporation owing to reflux).

It was therefore an object of the present invention to provide a process for separating acrylic acid and benzoic acid present as the main product and by-product in a product gas mixture of a partial heterogeneously catalyzed gas phase oxidation of a $C_3$ precursor compound of acrylic acid, which does not require the aforementioned energy-intensive separation method.

Accordingly, the process is provided for separating acrylic acid and benzoic acid present as the main product and by-product as well as other product gas mixture constituents in a product gas mixture of a partial heterogeneously catalyzed gas phase oxidation of a $C_3$ precursor compound of acrylic acid, in which the acrylic acid and the benzoic acid, together with other constituents of the product gas mixture which have lower and higher boiling points than acrylic acid, are converted from the product gas mixture to a liquid phase P, and constituents having a lower boiling point than benzoic acid and acrylic acid (based on the boiling point of the pure substances at 1 atm) (but no benzoic acid; "no" here means less than 10% by weight, preferably less than 5% by weight, even better less than 3% by weight or less than 2% by weight or less than 1% by weight, and at best less than 0.75% by weight, or less than 0.1% by weight, or 0% by weight, based in each case on the benzoic acid content of the liquid phase P) are removed from the resulting liquid phase P using at least one thermal separating process to leave a liquid phase P* which comprises at least 80% by weight of acrylic acid and, based on the amount of acrylic acid present, at least 0.1 per mille by weight (frequently at least 0.2 per mille by weight, or at least 0.3 per mille by weight, or at least 0.4 per mille by weight, or at least 0.5 per mille by weight, or at least 0.75 per mille by weight, or at least 1 per mille by weight) of benzoic acid, which comprises separating the benzoic acid from the acrylic acid by crystallization out of the liquid phase P*, the acrylic acid accumulating in the crystals formed and the benzoic acid in the remaining mother liquor.

The process according to the invention is based on the surprising finding that the depletion coefficient $A^{BZA}$ (based on the process) associated with the crystallization is regularly $\geq 15$. The depletion coefficient $A^{BZA}$ is generally understood to mean the quantitative ratio of benzoic acid remaining in the mother liquor to benzoic acid remaining in the crystals (in each case expressed as % by weight based on the total amount of mother liquor or the total amount of crystals). A crystal/mother liquor removal to an extent of more than 90% by weight, preferably to an extent of more than 95% by weight, or 97 or 98, or 99% by weight of its total amount is generally sufficient to determine $A^{BZA}$ (the influence of the residual moisture content on the crystals is generally negligible). An $A^{BZA}$ of $\geq 15$ demonstrates that there is essentially no incorporation of the benzoic acid into the crystals in the formation of the acrylic acid crystals. This forms the basis of the marked efficiency of the inventive procedure.

In the case of diacrylic acid ($A^{DA}$), acetic acid ($A^{AA}$) and propionic acid ($A^{PA}$) as acrylic acid secondary components, the corresponding depletion coefficient is typically at values of $\leq 10$. In other words, they are also incorporated into the acrylic acid crystals and can be extracted from these crystals only with difficulty, for example, by suitable washing.

In other words, a crystallizative removal of these impurities from acrylic acid generally requires the use of less efficient and more capital-intensive multistage crystallization processes, as recommended, for example, in EP-A 616998 in the form of a multistage combination of dynamic and static crystallization, and requires there as well as the multistage process, at least one dynamic and at least one static crystallizer. At best, under particular boundary conditions of the crystallization (cf. in particular WO 03/078378 and WO 01/77056), acrylic acid crystals are formed from which acetic acid and propionic acid can be removed comparatively efficiently by subsequent washing with pure acrylic acid melt. The greater $A^{BZA}$ is, the more attractive is a crystallizative removal of the benzoic acid from acrylic acid.

With the aforementioned experimental findings, the inventive procedure opens up the possibility, on the route to acrylic acid suitable for superabsorbents, of essentially quantitatively removing the benzoic acid contamination, which obstructs such a use, of the liquid phase P* in a crystallization stage with subsequent washing of the crystals with prepurified acrylic acid melt.

The wording "acrylic acid as the main product" and "benzoic acid as the by-product" in this document is intended to mean merely that the product gas mixture of the partial oxidation comprises significantly more acrylic acid than benzoic acid. In other words, acrylic acid is the desired target product of the partial oxidation, while benzoic acid is a basically undesired by-product thereof.

The process according to the invention is applicable in particular to those liquid phases P*, whose acrylic acid content is at least 85% by weight, or at least 90% by weight, or at least 95% by weight, or at least 96% by weight, or at least 97% by weight, or at least 98% by weight, or at least 99% by weight, or at least 99.5% by weight or more.

In this process, at all aforementioned (and of course also at a content of 80% by weight of acrylic acid in the liquid phase P*) acrylic acid contents of liquid phase P*, the content of benzoic acid based on the amount of acrylic acid present may, for example, in each case be from 0.1 to 20 per mille by weight, or 0.2 to 15 per mille by weight, or 0.3 to 10 per mille by weight, or from 0.4 to 8 per mille by weight, or from 0.5 to 6 per mille by weight, or from 0.75 to 4 per mille by weight, or from 1 to 3 per mille by weight. In general, the benzoic acid content of the liquid phase P*, based on acrylic acid present therein, is not greater than 100 per mille by weight, frequently not greater than 75 per mille by weight, or not greater than 50 per mille by weight. The use of the process according to the invention is advantageous especially when the content in the liquid phase P* of benzoic acid (is not 0 and) is at least 50% by weight, or at least 75% by weight, or at least 100% by weight, or at least 125% by weight, or at least 150% by weight, or at least 175% by weight, or at least 200% by weight, or at least 250% by weight, or at least 300% by weight, or at least 400% by weight, or at least 500% by weight of the weight of benzaldehyde present in the liquid phase P*. Of course, the liquid phase P* to be treated in accordance with the invention may also not comprise any benzaldehyde.

The process according to the invention is of particular significance when it is practiced in such a way that mother liquor remaining in the crystallizative removal (out of the liquid phase P*) is recycled at least partly into at least one of the thermal separating processes employed to obtain the liquid phase P* from the liquid phase P and/or into at least one of the processes employed for the combined conversion of the acrylic acid and benzoic acid present in the product gas mixture of the gas phase partial oxidation to the liquid phase P (normally below the top of the separating columns comprising separating internals used).

The basic structure of such a combined use of the distinct separating process of crystallization and of indistinct separating processes for obtaining the liquid phase P* from the product gas mixture of the heterogeneously catalyzed partial gas phase oxidation of the at least one $C_3$ precursor compound is known from DE-A 19606877.

An indistinct separating process is defined as a separating process in which the composition of the phase which comprises enriched target product and is formed when the separating process is employed is dependent to a marked degree on the composition of the mixture to be separated, while the inventive crystallizative treatment is a distinct separating process to the extent that the composition of the acrylic acid crystals which form is largely independent (ideally completely independent) of the composition of the liquid phase P*. In other words, in the distinct separating process of crystallization, a single establishment of equilibrium is sufficient from a thermodynamic point of view to achieve the desired separating action, while, in indistinct separating processes, several successive establishments of equilibrium have to be passed through from a thermodynamic point of view (see: McCabe-Thiele separating stages), in order to bring about a significant separating action.

In the case of such a combination of a distinct separating process and of at least one indistinct separating process, the process according to the invention is of increased significance in the respect that, in the continuous operation of such a procedure, the benzoic acid accumulates in the liquid phase P* to be treated in accordance with the invention as a result of the mother liquor recycling, since the mother liquor comprises the benzoic acid in enriched form. In other words, even comparatively low benzoic acid contents in the product gas mixture of the partial heterogeneously catalyzed gas phase oxidation can thus grow to become a serious problem which can only be dealt with sensibly by virtue of $A^{BZA}$ (based on the process) regularly being $\geq 15$ in accordance with the inventive finding. In the case of depletion coefficients $A^{BZA}$ of <15 a procedure to be practiced as described would be extremely inefficient. The efficiency required, especially on the industrial scale, is gained only by virtue of $A^{BZA}$ in the process according to the invention regularly being $\geq 15$.

However, the fact just mentioned is also relevant when mother liquors obtained in the process according to the invention, for the purpose of increasing the yield, are crystallized further, or when benzoic acid-comprising secondary streams occurring in the indistinct separating process are likewise treated by crystallization to increase the yield.

The inventive crystallizative treatment of the liquid phase P* is in principle subject to no restriction, including the process for removing the mother liquor from the crystals (all mother liquor/crystal removal processes detailed in the prior art documents cited can be employed).

In other words, it may be carried out in one or more stages, continuously or batchwise. In particular, it may also be carried out as a fractional crystallization. Typically, in a fractional crystallization, all stages which generate acrylic acid crystals which are purer (especially freer from benzoic acid) than the liquid phase P* supplied are known as purification stages and all other stages stripping stages. Appropriately, multistage processes are operated by the countercurrent principle, in which, after the crystallization in each stage, the crystals are removed from the mother liquor and these crystals of the particular stage are fed with the next highest degree of purity, while the crystallization residue of the particular stage is fed with the next lowest degree of purity.

In general, the temperature of the liquid phase P* during the crystallizative removal is between $-25°$ C. and $+14°$ C., in particular between $+12°$ C. and $-5°$ C.

For example, the process according to the invention may be performed as a layer crystallization (cf. DE-A 2606364, EP-A 616998, EP-A 648520 and EP-A 776875). In this crystallization, the crystals are frozen out in the form of continuous, firmly adhering layers. The deposited crystals are separated from the remaining residual melt (the mother liquor) by virtue of the residual melt simply flowing off. In principle, a distinction is drawn between "static" and "dynamic" layer crystallization processes. A characteristic feature of dynamic layer crystallization of liquid phases P* is forced convection of the liquid phase P*. This can be effected by pumped circulation of the liquid phase P* through tubes with full flow-through, by introduction of the liquid phase P* as a trickle film (for example according to EP-A 616998) or by introduction of inert gas into a liquid phase P* or by pulsation.

In the static processes, the liquid phase P* is at rest (for example in tube bundle or plate heat exchangers) and deposits in layers as result of slow temperature reduction on the secondary side. Afterward, the residual melt (mother liquor) is discharged, more highly contaminated fractions are sweated off from the crystal layer by slow temperature increase and the pure product is subsequently melted off (cf. WO 01/77056).

According to the invention, the inventive crystallization step, in the case of all liquid phases P* described in this document, will, however, preferably be performed according to the teaching of WO 01/77056, WO 02/055469 and WO 03/078378 as a suspension crystallization.

In general, a crystal suspension comprising suspended acrylic acid crystals is obtained by cooling the liquid phase P*, the acrylic acid crystals having a lower benzoic acid content and the remaining residual melt (mother liquor) a higher benzoic acid content (relatively, based on the particular total amount) than the liquid phase P* to be purified. The acrylic acid crystals may grow directly in suspension and/or be deposited as a layer on a cooled wall from which they are subsequently scratched off and resuspended in the residual melt (mother liquor).

All suspension crystallizers and suspension crystallization processes detailed in WO 01/77056, WO 02/055469, WO 03/078378 and in Research Disclosure Database Number 496005 (published in August 2005) are useful in accordance with the invention. In general, the acrylic acid crystal suspension generated has a solids content of from 20 to 40% by weight.

In addition, all processes specified in the aforementioned WO publications are useful for the separation of suspension crystals which have formed and mother liquor which remains (for example mechanical separating processes such as centrifugation). Preference is given in accordance with the invention to separating in a wash column.

This is preferably a wash column with forced transport of the deposited acrylic acid crystals. The crystal volume fraction in the crystal bed generally attains values of $\geq 0.5$. In general, the wash column is operated at values of from 0.6 to 0.75. The wash liquid used is advantageously the melt of acrylic acid crystals purified (removed) beforehand in the wash column. The washing is normally effected in countercurrent. The process according to the invention thus in particular comprises processes which comprise the following process steps:

a) crystallization of acrylic acid out of a liquid phase P*;
b) separation of the acrylic acid crystals from the remaining mother liquor (residual melt, liquid residual phase);
c) at least partial melting of the acrylic acid crystals removed and
d) at least partial recycling of the molten acrylic acid crystals to step b) and/or to step a).

Preference is given to effecting step b) by countercurrent washing with acrylic acid crystals which have been removed beforehand, melted and recycled into step b).

Advantageously in accordance with the invention (but not necessarily), the liquid phase P* comprises water when the process according to the invention is employed, since formation of acrylic acid crystals in the presence of water, according to the teaching of WO 01/77056 and WO 03/078378, causes a particularly favorable crystal form for the subsequent separation of the crystals from the remaining mother liquor. This is especially true when the crystallization is performed as a suspension crystallization, and even more true when the subsequent mother liquor removal is performed in a wash column, and even more true when the wash liquid used is the melt of acrylic acid crystals which have already been purified in the wash column.

In other words, the process according to the invention comprises in particular processes in which the liquid phase P* to be treated by crystallization is converted under the action of cold conditions to a crystal suspension consisting of acrylic acid crystals and liquid residual phase (residual melt), the proportion by weight of benzoic acid in the acrylic acid crystals being smaller and the proportion by weight of the liquid residual phase (the mother liquor) of benzoic acid being greater than the proportion by weight of benzoic acid in the liquid phase P*, a portion of the remaining mother liquor is removed mechanically if appropriate from the crystal suspension, and the acrylic acid crystals are freed in a wash column of remaining mother liquor, with the proviso that a) the liquid phase P*, based on the acrylic acid present therein, comprises at least 50 ppm by weight or from 0.20 to 20% by weight, often to 15 or to 10% by weight, of water, and
b) the wash liquid used is the melt of acrylic acid crystals purified in the wash column.

Moreover, it is advantageous in accordance with the invention when the water content of the liquid phase P* in the above-described procedures (or quite generally when the process according to the invention is employed), based on acrylic acid present in the liquid phase P*, is from 0.2 or 0.4 to 8, or to 10, or to 20% by weight.

All of the aforementioned applies in particular when the wash column is a wash column with forced transport of the acrylic acid crystals, in particular when it is a hydraulic or a mechanical wash column according to WO 01/77056 and is operated as detailed therein.

All of the aforementioned is true in particular when the wash column is designed and operated according to the teachings of WO 03/041832 and of WO 03/041833.

In principle, the heterogeneously catalyzed partial gas phase oxidation before the use of the separating process according to the invention can be performed in such a way as is known from the prior art (apart from the fact that the crude $C_3$ precursor compound used to obtain the starting reaction gas mixture may have a lower purity).

In other words, it can be performed, for example, as described in DE-A 10351269, DE-A 10245585, DE 1020050227988, EP-A 1695954, DE-A 10351269, EP-A 990636, EP-A 1106598, DE-A102005010111, DE-A 1020050130399, DE-A 102004025445, DE-A 102004021764, DE-A 10338529, DE-A 10337788, DE-A 10360396, DE-A 10316465, DE-A10313210, DE-A10313214, DE-A10313213, DE-A 10313212, DE 102005062026.4, DE-A 10313211, DE-A 10313208 and DE-A 10313209, and the prior art described in these documents.

In particular, the process according to the invention is applicable to the product gas mixture of a two-stage heterogeneously catalyzed partial gas phase oxidation of propylene to acrylic acid. In the first reaction stage, the propylene is essentially partially oxidized to acrolein, and, in the second reaction stage, the acrolein obtained in the first reaction stage is partially oxidized to acrylic acid. Typically, the acrolein, as a constituent of the product gas mixture of the first reaction stage, if appropriate supplemented by molecular oxygen or by a mixture of molecular oxygen and inert gas, is fed to the second reaction stage.

The process according to the invention is relevant in particular when the propylene conversion $U^P$ in the propylene partial oxidation is $\geq 91$ mol %, or $\geq 92$ mol %, or $\geq 93$ mol %, or $\geq 94$ mol %, or $\geq 95$ mol %, or $\geq 96$ mol %, or $\geq 97$ mol %, or $\geq 98$ mol %, or $\geq 99$ mol %.

The process according to the invention is also relevant in particular when the acrolein conversion $U^A$ in the acrolein partial oxidation is $\geq 96$ mol %, or $\geq 97$ mol %, or $\geq 98$ mol %, or $\geq 98.5$ mol %, or $\geq 99$ mol %, or $\geq 99.5$ mol %, or $\geq 99.8$ mol % or more.

This is because aforementioned conversions (they are always based on single pass of the reaction gas mixture through the catalyst bed), when the same catalyst system is used, are normally achieved when the reaction temperature in the particular reaction stage is selected at an elevated level and/or a catalyst charge comprising catalysts having elevated activity is used. Both promote benzoic acid by-production.

The aforementioned is true in particular in the case of the two-stage partial oxidation of propylene to acrylic acid already addressed.

The catalyst bed for the heterogeneously catalyzed partial oxidation of the $C_3$ precursor compound will generally be a fixed bed. Particularly active (fixed bed) catalysts for the propylene partial oxidation are those whose active composition is a multimetal oxide composition whose specific surface is from 0.1 to 120 $m^2/g$, or from 0.2 to 50 $m^2/g$, or from 1 to 20 $m^2/g$, or from 2 to 10 $m^2/g$.

In addition, regarding the activity of the (fixed bed) catalysts of the propylene partial oxidation to acrolein, it is favorable when the numerically most common pore diameter of their multimetal oxide active composition is from 0.1 to 1 μm.

Elevated activity of the (fixed bed) catalysts for the partial oxidation of propylene to acrolein is present especially when the aforementioned numerically most common pore diameter and one of the aforementioned specific surface areas are present in combination with the multimetal oxide active composition.

The total pore volume of the aforementioned multimetal oxide active compositions (catalysts) with elevated activity is advantageously at the same time from 0.1 to 1.00 ml/g, usually from 0.10 to 0.80 ml/g, or from 0.20 to 0.40 ml/g.

Frequently, it is even sufficient when the catalysts for the heterogeneously catalyzed partial oxidation of propylene to acrolein comprise aforementioned catalysts.

Particularly active (fixed bed) catalysts for the acrolein partial oxidation (especially as the second reaction stage of a two-stage propylene partial oxidation to acrylic acid) are those whose active composition is a multimetal oxide composition whose specific surface area is from 0.1 to 150 $m^2/g$, or from 0.2 to 50 $m^2/g$, or from 1 to 20 $m^2/g$ or from 2 to 10 $m^2/g$.

In addition, regarding the activity of the (fixed bed) catalysts of the acrolein partial oxidation to acrylic acid, it is favorable when the numerically most common pore diameter of their multimetal oxide active composition is from 0.1 to 1 μm.

Elevated activity of the (fixed bed) catalysts for the partial oxidation of acrolein to acrylic acid is present especially when the aforementioned numerically most common pore diameter and one of the aforementioned specific surface areas are present in combination with the multimetal oxide active composition.

The total pore volume of the aforementioned multimetal oxide active compositions (catalysts) with elevated activity is advantageously at the same time from 0.1 to 0.90 ml/g, usually from 0.20 to 0.80 ml/g, or from 0.30 to 0.70 ml/g.

Frequently, it is even sufficient when the catalysts for the heterogeneously catalyzed partial oxidation of acrolein to acrylic acid comprise aforementioned catalysts.

In principle, in the two partial oxidations detailed above, the volume-specific activity of the catalyst bed (especially fixed catalyst bed) in flow direction of the reaction gas mixture may be constant over the length of the flow path. However, particular relevance for the process according to the invention arises when this volume-specific activity of the (fixed) catalyst bed increases at least once (continuously or abruptly, or stepwise) in flow direction of the reaction gas mixture in the particular case. In all aforementioned cases, it is also advantageous when the active composition does not change over the length of the flow path.

The aforementioned catalysts may either be coated catalysts or unsupported catalysts. The geometry of the catalysts may in principle be as desired. It is possible to use spheres, polygons, solid cylinders or rings. The longest dimension of the shaped catalyst bodies is appropriately from 1 to 10 mm, or from 2 to 8 mm. This is understood to mean the longest direct line connecting two points on the shaped catalyst body surface. The volume-specific activity of the fixed catalyst bed can be brought about by appropriate dilution of the catalysts with essentially inert shaped bodies (shaped diluent bodies). Their geometry can essentially correspond to that of the shaped catalyst bodies. Useful materials for such inert shaped bodies are in principle all of those which are also suitable as a support material for coated catalysts suitable in accordance with the invention. Such materials are in particular nonporous oxides such as aluminum oxides, silicon dioxide, thorium dioxide, zirconium dioxide, silicon carbide, silicates such as magnesium silicate or aluminum silicate, or steatite.

Multimetal oxide active compositions for catalysts for the propylene→acrolein partial oxidation with elevated activity comprise, appropriately in accordance with the invention, the metal elements Mo, Fe and Bi. They are of particularly elevated activity when their stoichiometry satisfies the following formula I:

$$Mo_{12}Bi_aFe_bX^1_cX^2_dX^3_eX^4_fO_n \qquad (I)$$

where
$X^1$=nickel and/or cobalt
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements other than oxygen in (I).

The aforementioned is especially true when the active composition has the properties already addressed regarding specific surface area and pore volume.

Multimetal oxide active compositions for catalysts for the acrolein→acrylic acid partial oxidation with elevated activity comprise, appropriately in accordance with the invention, the metal elements Mo and V. They are of particularly elevated activity when their stoichiometry satisfies the following formula II:

$$Mo_{12}V_aX^1_bX^2_cX^3_dX^4_eX^5_fX^6_gO_n \qquad (II)$$

where
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one of more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements other than oxygen in (II).

Particularly active embodiments among the active multimetal oxides (II) are those which are encompassed by the following definitions of the variables of the general formula II:

$X^1$=W, Nb and/or Cr,
$X^2$=Cu, Ni, Co and/or Fe,
$X^3$=Sb,
$X^4$=Na and/or K,
$X^5$=Ca, Sr, and/or Ba,
$X^6$=Si, Al and/or Ti,
a=from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements other than oxygen in (II).

Advantageously, the partial heterogeneously catalyzed gas phase oxidations of a $C_3$ precursor compound are performed in tube bundle reactors. The fixed catalyst bed is disposed in the reaction tubes of the tube bundle reactor. The catalyst tubes are flowed around by a liquid heat carrier (generally a metal melt or a liquid metal), in order to remove the heat of reaction.

The loading of the (fixed) catalyst bed with propylene or acrolein in both cases may be $\geq$70 l (STP)/l·h or $\geq$90 l (STP)/l·h, or $\geq$110 l (STP)/l·h, or $\geq$130 l (STP)/l·h, or $\geq$140 l (STP)/l·h, or $\geq$160 l (STP)/l·h, or $\geq$180 l (STP)/l·h, or $\geq$240 l (STP)/l·h, or $\geq$300 l (STP)/l·h.

In general, it is, however, $\leq$600 l (STP)/l·h (the loading values are based in each case on the volume of the fixed catalyst bed, excluding any additionally used sections which consist exclusively of inert material.

In this document, the loading of the (fixed) catalyst bed with starting reaction gas mixture is understood to mean the amount of starting reaction gas mixture in standard liters (l (STP); the volume in liters that the corresponding amount of starting reaction gas mixture would take up under standard conditions, i.e. at 25° C. and 1 bar) which is conducted through one liter of (fixed) catalyst bed per hour. The loading of the (fixed) catalyst bed can also be based only on one component of the starting reaction gas mixture. In that case, it is the amount of this component in standard liters which is conducted through one liter of the (fixed) catalyst bed per hour as a constituent of the corresponding starting reaction gas mixture.

In this document, inert gases are understood quite generally to be those gases which, in the course of the partial oxidation, in each case alone, remain chemically unchanged to an extent of at least 95 mol %, preferably to an extent of at least 97 mol % and most preferably to an extent of 99 mol % or more.

The reaction temperature in the propylene→acrolein partial oxidation is generally from 270 to 450° C. or from 280 to 420° C., preferably from 300 to 380° C. The reaction temperature in the acrolein→acrylic acid partial oxidation is generally from 200 to 370° C. or from 200 to 320° C., preferably from 220 to 300° C.

The working pressure in the inventive partial oxidations may generally be either below standard pressure (for example up to 0.5 atm; the reaction gas mixture is sucked through) or above standard pressure. Typically, the working pressure will be at values of from 1 to 5 atm, frequently from 1.5 to 3.5 atm. Normally, the working pressure in the inventive partial oxidations will not exceed 100 atm.

A useful source for the molecular oxygen required as an oxidizing agent in the course of the partial oxidations is either air or air depleted in molecular nitrogen.

The catalysts to be used for the inventive partial oxidation of propylene (to acrolein) or acrolein (to acrylic acid) are generally selected such that the selectivity of target product formation (acrolein or acrylic acid) is generally $\geq$83 mol %, frequently $\geq$85 mol %, or $\geq$88 mol %, often $\geq$90 mol %, or $\geq$93 mol % or more.

Typical starting reaction gas mixtures for the propylene partial oxidation (to acrolein) may, for example comprise:
from 5 to 12% by volume of propylene,
from 2 to 15% by volume of water,
from $\geq$0 to 10% by volume of propane,
from $\geq$0.1 to 5% by volume of constituents other than propylene, propane, water, oxygen and nitrogen
and sufficient molecular oxygen, that the molar ratio of molecular oxygen to propylene is from 1 to 3, and
as the remainder up to 100% by volume of the total amount, molecular nitrogen.

Alternatively, the starting reaction gas mixture for the propylene partial oxidation (to acrolein) may comprise:
from 6 to 10% by volume of propylene,
from 8 to 18% by volume of molecular oxygen,
from 6 to 30% by volume of propane and
from 32 to 72% by volume of molecular nitrogen.

Reaction mixtures for the propylene→acrolein partial oxidation can also comprise up to 20% by volume of $H_2$.

Starting reaction gas mixtures for the acrolein partial oxidation (to acrylic acid) comprise, for example:
from 4 to 8% by volume of acrolein,
from 2 to 9% by volume of molecular oxygen,
from 0 to 30% by volume of propane,
from 30 to 75% by volume of molecular nitrogen and
from 5 to 30% by volume of steam, or from 3 to 25% by volume of acrolein,
from 5 to 65% by volume of molecular oxygen,
from 6 to 70% by volume of propane,
from 0 to 20% by volume of molecular hydrogen and
from 5 to 65% by volume of steam.

Partial oxidations particularly relevant in accordance with the invention are those of propylene (to acrolein) or of acrolein (to acrylic acid), in which the product gas mixture still comprises from $\geq$0 to 4% by volume (for example to 0.5% by volume, or to 1% by volume, or to 1.5% by volume, or to 2% by volume, or to 2.5% by volume) of molecular oxygen.

In principle, the organic contents in the liquid phase P* of its constituents can be determined by gas chromatography.

For the conversion of the acrylic acid and benzoic acid present in the product gas mixture of the partial oxidation to be performed in accordance with the invention to the liquid phase P, absorptive and/or condensative measures are useful in principle.

Examples of useful absorbents include water, aqueous solutions (these may comprise, for example, from 0.1 to 10% by weight of acetic acid, 0.1 to 5% by weight of acrylic acid and from 80 to 99.8% by weight of water) and/or organic (especially hydrophobic) solvents (e.g. diphenyl ether, diphenyl and/or dimethyl phthalate). Before the absorption, the product gas mixture of the partial oxidation may, appropriately from an application point of view, also be subjected to a direct and/or indirect cooling.

Absorption and/or condensation processes suitable in accordance with the invention, are described, for example in the documents DE-A 10336386, WO 01/96271, DE-A 19631645, DE-A 19501325, EP-A 982289, DE-A 19838845, WO 02/076917, EP-A 1695954, EP-A 695736, EP-A 778225, EP-A 1041062, EP-A 982287, EP-A 982288, US 2004/0242826, EP-A 792867, EP-A 784046, EP-A 695736, EP-A 1125912, EP-A 1388533 and the literature cited on this subject in these documents.

The acrylic acid and benzoic acid present in the product gas mixture can, though, for example also be liquefied by condensing the constituents having a higher boiling point than water in the product gas mixture.

Both the absorptive and the condensative conversion of the acrylic acid and benzoic acid to the liquid phase P, like their conversion to the liquid phase P*, are typically undertaken in separating columns comprising separating internals (to increase the exchange surface area).

Absorption and condensation can also be employed superimposed on one another.

Separating columns suitable with regard to the aforementioned absorption and/or condensation processes are disclosed in particular in DE-A 10336386, EP-A 1125912 and US 2004/0242826 A1.

Useful separating internals are in principle all internals known to be separation-active. In other words, it is possible to use trays such as bubble-cap trays, dual-flow trays or valve trays, random packings, for example Raschig rings, or structured packings, for example Sulzer packings, as separating internals.

In the separating column, the product gas mixture, if appropriate cooled beforehand, of the partial oxidation is generally conducted from the bottom upward in an ascending manner. In an absorptive condensation, the absorbent in the separating column is normally moved (conducted) from the top downward.

The liquid phase P* comprising acrylic acid and benzoic acid can be withdrawn from the separating column, appropriately from an application point of view, from the liquid column bottoms or via liquid side drawer removal below the feed of the product gas mixture which has been cooled if appropriate.

Using at least one thermal separating process, constituents having a lower boiling point (based on atmospheric pressure) than benzoic acid and acrylic acid are now removed from the liquid phase P.

Advantageously, in accordance with the invention, the at least one thermal separating process is employed such that the low boiler removal captures those constituents of the liquid phase P whose boiling point, as a pure substance and at atmospheric pressure, is ≦the boiling point of water.

A thermal separating process to be employed particularly favorably is stripping with a gas (e.g. air, molecular nitrogen or another gas).

To this end, this gas is conducted through the liquid phase P (advantageously from an application point of view in countercurrent in a separating column comprising separating internals) and strips low-boiling constituents present therein out of it. Advantageously, the liquid phase P is heated beforehand for this purpose. Appropriately, the stripping is effected at a working pressure below atmospheric pressure.

As a result of the latter measure, the stripping has a desorption superimposed on it. It will be appreciated that the desorption can also be used alone for the low boiler removal.

Alternatively to the stripping and/or desorption, or else thereafter, a rectificative low boiler removal can be performed. Especially with a view to fixing the separating line at the boiling point of water, it is appropriate to perform the rectificative low boiler removal at least partly as an azeotropic rectification. Examples of azeotroping agents suitable in this regard include heptane, dimethylcyclohexane, ethylcyclohexane, toluene, ethylbenzene, octane, chlorobenzene, xylene or mixtures (for example those of 60% by weight of toluene and 40% by weight of heptane) thereof. Alternative azeotroping agents which may be used are also methyl isobutyl ketone or isopropyl acetate.

Further suitable azeotroping agents are disclosed in US 2004/0242826, EP-A 778255, EP-A 695736 and the prior art cited in these documents. Typically aforementioned rectifications are likewise advantageously performed at working pressures below atmospheric pressure. It will be appreciated that each of the aforementioned thermal separating processes can be employed either alone or in combination with one or more of the other thermal separating processes mentioned.

Since, in accordance with the invention, thermal separating processes are employed advantageously merely for the purpose of low boiler removal, the inventive procedure is accompanied, as a further advantage, by a particularly minor degree of undesired polymer formation and/or a particularly low demand for polymerization inhibitors.

However, it will be appreciated that all process steps detailed in this document are performed with polymerization inhibition. The procedure may be as described in the prior art cited. An outstanding position among the entirety of the available acrylic acid process stabilizers is occupied by dibenzo-1,4-thiazine (PTZ), 4-hydroxy-2,2,6,6-tetramethylpiperidine 1-oxyl (4-OH-TEMPO) and p-methoxyphenol (MEHQ), which may be part of the mixtures to be treated in accordance with the invention, especially of liquid phases, in each case alone, or in pairs, or as a ternary mixture. Typically, the total amount of polymerization inhibitors present in liquid phases comprising acrylic acid, based on the total amount of acrylic acid present therein, is from 0.001 to 2% by weight.

After performing the low boiler removals described, what generally remains is a liquid phase P* which comprises at least 80% by weight of acrylic acid and, based on the amount of acrylic acid present, at least 0.1 per mille by weight of benzoic acid. Based on the acrylic acid present in the liquid phase P* it advantageously comprises at least 50 ppm by weight or at least 0.2% by weight, or from 0.2 to 15% by weight of water.

Owing to undesired formation of acrylic acid oligomers (Michael adducts) in the liquid phases comprising acrylic acid when they are left alone, the inventive crystallizative removal is employed as far as possible immediately after the liquid phase P* is obtained. Thermal dissociation of the acrylic acid oligomers which are likewise accumulated in the mother liquors allows the acrylic acid present therein to be recovered and recycled into one of the thermal separating processes employed to obtain the liquid phase P and/or P*.

In general, the process according to the invention will be followed by a process in which acrylic acid crystals are melted and free-radically polymerized to polymers. Frequently, the aforementioned polymers will be superabsorbing polyacrylates.

EXAMPLES

A stirred tank which had a capacity of 2 liters was used. The geometry of the stirred tank was cylindrical, with an internal diameter of 110 mm. The stirred tank was manufactured from glass. However, the bottom of the stirred tank was manufactured in jacketed form from stainless steel. The stainless steel wall thickness was 2 mm. The separation of the two walls was approx. 1 cm. The space between the two walls was flowed through by a mixture consisting of 30% by weight of water, 40% by weight of methanol and 30% by weight of ethylene glycol as a cooling medium (at least 75 l/h).

The contents of the stirred tank were stirred by means of a twin-paddle stirrer (the paddle height was 50 mm, the diameter 57 mm, and the rotational speed was 500 rpm).

In all experiments, the stirred tank was filled with from 1500 to 1650 g of glacial acrylic acid whose acrylic acid content was ≧99.5% by weight and which had been doped with different contents of benzoic acid (its temperature was 25° C.). Its water content was 148 ppm by weight. In addition, the glacial acrylic acid had been polymerization-inhibited by a content of approx. 250-270 ppm by weight of phenothiazine (PTZ). The temperature of the cooling medium (in each case proceeding from a start temperature of 11° C.) was lowered continuously with cooling rates of from 15 K/h to 60 K/h.

The crystallization process was interrupted in each case once a crystal layer having a mass M of layer thickness d of approx. 10 mm had been deposited on the tank bottom. The stirred tank was mounted to be rotatable. With interruption of the crystallization process, the stirred tank was turned on its head in order to allow the remaining mother liquor (mother acid) to flow out. Subsequently, the mother liquor which had flowed out and the deposited crystals were each analyzed for their benzoic acid content, and the particular depletion coefficient $A^{BZA}$ was determined from the analysis results.

The results achieved are shown in the table below. It additionally shows the crystal growth rate W in mm/min and the cooling time t in min.

U.S. Provisional Patent Application No. 60/852,674, filed Oct. 19, 2006, is incorporated into the present patent application by literature reference.

With regard to the abovementioned teachings, numerous changes and deviations from the present invention are possible. It can therefore be assumed that the invention, within the scope of the appended claims, can be performed differently from the way described specifically herein.

TABLE

| | Benzoic acid content (‰ by wt.) | % by wt. of PTZ | Cooling rate (K/h) | d (mm) | M (g) | W (mm/min) | T (min) | $A^{BZA}$ |
|---|---|---|---|---|---|---|---|---|
| Sample A | 1 | 270 | 15 | 12.9 | 161.2 | 0.152 | 85 | 54.1 |
| Sample B | 1.5 | 270 | 30 | 7.2 | 89.9 | 0.206 | 35 | 31.5 |
| Sample C | 1.5 | 270 | 60 | 10.8 | 120.7 | 0.300 | 36 | 30.3 |

Allyl acrylate, benzaldehyde, coumarone and furfurals, as acrylic acid impurities, likewise regularly have depletion coefficients A of >>20. In contrast, the depletion coefficients A for diacrylic acid, acetic acid and propionic acid as acrylic acid impurities are at values of <10. The high depletion coefficient found for benzoic acid is surprising against this background.

The invention claimed is:

1. A process for separating acrylic acid and benzoic acid present as the main product and bi-product as well as other product gas mixture constituents in a product gas mixture of a partial heterogeneously catalyzed gas phase oxidation of a $C_3$ precursor compound of acrylic acid, in which the acrylic acid and the benzoic acid, together with other constituents of the product gas mixture which have lower and higher boiling points than acrylic acid, are converted from the product gas mixture to a liquid phase P, and constituents having a lower boiling point than benzoic acid and acrylic acid are removed from the resulting liquid phase P using at least one thermal separating process to leave a liquid phase P* which comprises at least 80% by weight of acrylic acid and, based on the amount of acrylic acid present, at least 0.1 per mille by weight of benzoic acid, which comprises separating the benzoic acid from the acrylic acid by crystallization out of the liquid phase P*, the acrylic acid accumulating in the crystals formed and the benzoic acid in the remaining mother liquor.

2. The process according to claim 1, wherein the liquid phase P* comprises at least 90% by weight of acrylic acid.

3. The process according to claim 1, wherein the liquid phase P* comprises at least 95% by weight of acrylic acid.

4. The process according to claim 1, wherein the liquid phase P*, based on the amount of acrylic acid present, comprises at least 0.3 per mille by weight of benzoic acid.

5. The process according to claim 1, wherein the liquid phase P*, based on the amount of acrylic acid present, comprises at least 0.5 per mille by weight of benzoic acid.

6. The process according to claim 1, wherein the content in the liquid phase P* of benzoic acid is at least 50% by weight of the weight of benzaldehyde present in the liquid phase P*.

7. The process according to claim 1, wherein the content in the liquid phase P* of benzoic acid is at least 100% by weight of the weight of benzaldehyde present in the liquid phase P*.

8. The process according to claim 1, wherein the content in the liquid phase P* of benzoic acid is at least 150% by weight of the weight of benzaldehyde present in the liquid phase P*.

9. The process according to claim 1, wherein mother liquor remaining in the crystallizative removal is recycled at least partly into at least one of the thermal separation processes employed to obtain the liquid phase P* from the liquid phase P and/or into at least one process for the combined conversion of the acrylic acid and benzoic acid present in the product gas of the partial gas phase oxidation into the liquid phase P.

10. The process according to claim 1, wherein the crystallizative removal of the acrylic acid out of the phase P* is effected in one stage.

11. The process according to claim 1, wherein the crystallizative removal of the acrylic acid out of the phase P* is effected in more than one stage.

12. The process according to claim 1, wherein the crystallizative removal of the acrylic acid is effected by layer crystallization.

13. The process according to claim 1, wherein the crystallizative removal of the acrylic acid is effected by suspension crystallization.

14. The process according to claim 13, wherein the suspension crystals formed are separated from the remaining mother liquor in a wash column.

15. The process according to claim 14, wherein the wash liquid used is the melt of acrylic acid crystals removed beforehand in the wash column.

16. The process according to claim 1, which comprises:
a) crystallizing acrylic acid out of a liquid phase P*,
b) separating the acrylic acid crystals from the remaining mother liquor, c) at least partial melting of the acrylic acid crystals removed and d) at least partial recycling of the molten acrylic acid crystals to step b) and/or to step a).

17. The process according to claim 1, wherein the liquid phase P* comprises at least 150 ppm by weight of water.

18. The process according to claim 1, wherein the acrylic acid and benzoic acid present in the product gas mixture of the partial gas phase oxidation are converted by absorption by means of an aqueous solution.

19. The process according to claim 1, wherein the $C_3$ precursor compound is propylene.

20. The process according to claim 1, wherein the $C_3$ precursor compound is propane.

21. The process according to claim 1, wherein the $C_3$ precursor compound is acrolein and the acrolein conversion in the acrolein partial oxidation is $\geqq 99.5$ mol %.

22. The process according to claim 1, which is followed by a process in which acrylic acid crystals are melted and polymerized free-radically to polymers.

* * * * *